United States Patent
Tanaka et al.

(10) Patent No.: US 10,775,393 B2
(45) Date of Patent: Sep. 15, 2020

(54) REAGENT FOR PROTHROMBIN TIME MEASUREMENT, METHOD FOR PRODUCTION THEREOF, AND METHOD FOR MEASUREMENT OF PROTHROMBIN TIME

(71) Applicant: SYSMEX CORPORATION, Kobe-shi, Hyogo (JP)

(72) Inventors: Yusuke Tanaka, Kobe (JP); Takahiko Bando, Kobe (JP); Kiyoko Kohama, Kobe (JP); Haruki Yamaguchi, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 140 days.

(21) Appl. No.: 15/468,887

(22) Filed: Mar. 24, 2017

(65) Prior Publication Data

US 2017/0285046 A1   Oct. 5, 2017

(30) Foreign Application Priority Data

Mar. 30, 2016  (JP) .................................. 2016-068011

(51) Int. Cl.
| | | |
|---|---|---|
| G01N 33/86 | (2006.01) | |
| A61K 8/14 | (2006.01) | |
| A61K 51/12 | (2006.01) | |
| A61K 9/127 | (2006.01) | |

(52) U.S. Cl.
CPC ............... *G01N 33/86* (2013.01); *A61K 8/14* (2013.01); *A61K 9/127* (2013.01); *A61K 51/1234* (2013.01); *G01N 2333/7454* (2013.01); *G01N 2333/974* (2013.01)

(58) Field of Classification Search
CPC ..... G01N 2333/7454; G01N 2333/974; G01N 33/86; G01N 33/92; A61K 8/14; A61K 9/127; A61K 51/1234
See application file for complete search history.

(56) References Cited

U.S. PATENT DOCUMENTS

| | | | | |
|---|---|---|---|---|
| 5,314,695 | A | * | 5/1994 | Brown ................... A61K 9/127 424/450 |
| 6,100,072 | A | | 8/2000 | Brucato et al. |
| 6,203,816 | B1 | | 3/2001 | Brown |
| 6,248,353 | B1 | | 6/2001 | Singh |
| 2002/0182225 | A1 | | 12/2002 | Wang et al. |
| 2004/0086953 | A1 | | 5/2004 | Jenny et al. |
| 2005/0221414 | A1 | | 10/2005 | Varadi et al. |
| 2009/0104637 | A1 | | 4/2009 | Ismagilov et al. |

FOREIGN PATENT DOCUMENTS

| | | |
|---|---|---|
| CN | 101410049 A | 4/2009 |
| JP | 2001-255332 A | 9/2001 |
| JP | 2004-157122 A | 6/2004 |
| WO | 92/08479 A1 | 5/1992 |
| WO | 94/07515 A1 | 4/1994 |
| WO | 98/48283 A1 | 10/1998 |
| WO | 01/41740 A2 | 6/2001 |

OTHER PUBLICATIONS

S. A. Smith, Phospholipid composition controls thromboplastin sensitivity to individual clotting factors, Journal of Thrombosis and Haemostasis, 4: 820-827, 2006.*

Chinese Office Action dated Jun. 23, 2020 in a counterpart Chinese patent application No. 201710200741.8.

* cited by examiner

*Primary Examiner* — Rachael E Bredefeld
*Assistant Examiner* — Erinne R Dabkowski
(74) *Attorney, Agent, or Firm* — Sughrue Mion, PLLC

(57) ABSTRACT

Disclosed is a reagent for prothrombin time measurement, wherein the reagent contains a liposome composition containing a first liposome having a phospholipid layer, a second liposome having a phospholipid layer of a different composition from that of the first liposome, and tissue factor, wherein the tissue factor is associated with the phospholipid layer of at least one of the first liposome and the second liposome; the first liposome contains a phosphatidylcholine compound, a phosphatidylethanolamine compound, and a phosphatidylserine compound; and the second liposome contains at least one phospholipid selected from the group consisting of a phosphatidylcholine compound and a phosphatidylethanolamine compound.

11 Claims, 2 Drawing Sheets

REAGENT FOR PROTHROMBIN TIME MEASUREMENT, METHOD FOR PRODUCTION THEREOF, AND METHOD FOR MEASUREMENT OF PROTHROMBIN TIME

CROSS REFERENCE TO RELATED APPLICATIONS

This application claims priority from prior Japanese Patent Application No. 2016-068011, filed on Mar. 30, 2016, entitled "REAGENT FOR PROTHROMBIN TIME MEASUREMENT AND METHOD FOR PRODUCTION THEREOF", the entire contents of which are incorporated herein by reference.

TECHNICAL FIELD

The present invention relates to a reagent for prothrombin time measurement and a method for production thereof.

BACKGROUND

In measuring prothrombin time, use is made, for example, of a reagent for prothrombin time measurement that contains a tissue factor-containing liposome in which a recombinant tissue factor is associated with a liposome composed of phosphatidylcholine and phosphatidylserine (see, for example, WO 98/48283).

On the other hand, it has recently been proposed, from the viewpoint of the standardization of coagulation tests, that an appropriate range of clotting times and an appropriate international sensitivity index should be determined for reagents for prothrombin time measurement that are used for the assessment of prothrombin time.

However, when conventional reagents for prothrombin time measurement are used to determine the clotting time of normal plasma, there is a desire that these reagents result in measurements that meet both a clotting time within an appropriate range and an appropriate international sensitivity index.

The present invention provides a new reagent for prothrombin time measurement that can ensure measurements that are within an appropriate range of clotting times and have an appropriate international sensitivity index when the coagulation of normal plasma is measured, and a method for production thereof.

SUMMARY OF THE INVENTION

The scope of the present invention is defined solely by the appended claims, and is not affected to any degree by the statements within this summary.

A first aspect of the present invention encompasses a reagent for prothrombin time measurement, wherein the reagent contains a liposome composition containing a first liposome having a phospholipid layer, a second liposome having a phospholipid layer of a different composition from that of the first liposome, and a tissue factor, wherein the tissue factor is associated with the phospholipid layer of at least one of the first liposome and the second liposome; the first liposome contains a phosphatidylcholine compound, a phosphatidylethanolamine compound, and a phosphatidylserine compound; and the second liposome contains at least one phospholipid selected from the group consisting of a phosphatidylcholine compound and a phosphatidylethanolamine compound.

A second aspect of the present invention encompasses a method for producing a reagent for prothrombin time measurement, including steps of: (A) forming a first liposome having a phospholipid layer, using a phosphatidylcholine compound, a phosphatidylethanolamine compound, and a phosphatidylserine compound; (B) forming a second liposome having a phospholipid layer of a different composition from that of the first liposome, using at least one phospholipid selected from the group consisting of a phosphatidylcholine compound and a phosphatidylethanolamine compound; and (C) allowing a tissue factor to associate with the phospholipid layer of at least one of the first liposome obtained in step (A) and the second liposome obtained in step (B).

DETAILED DESCRIPTION OF THE PREFERRED EMBODIMENTS

1. Reagents for Prothrombin Time Measurement

Figure 1:
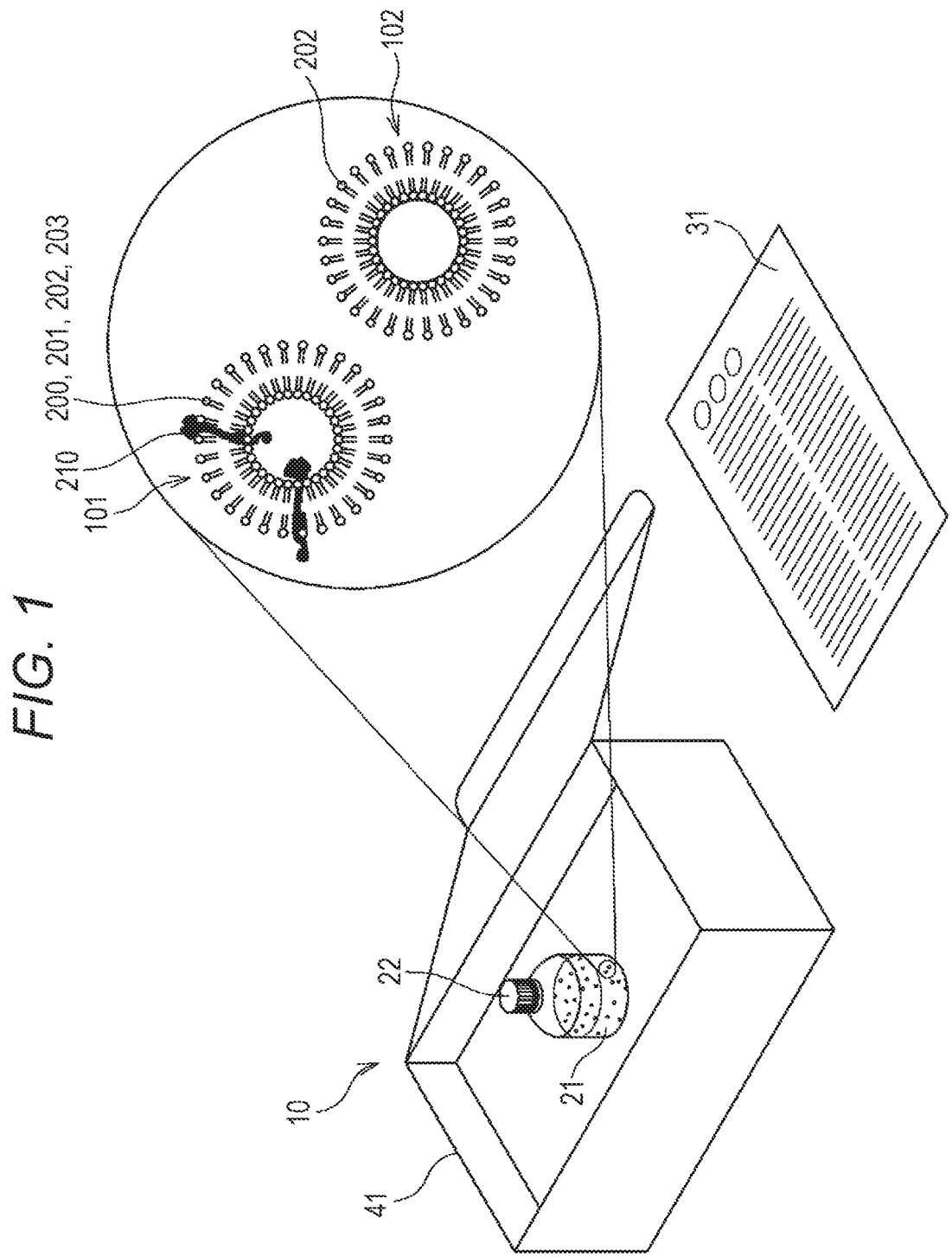
FIG. 1 is a schematic view illustrating the construction of a reagent kit.

A reagent for prothrombin time measurement according to an embodiment of the present invention (hereinafter referred to as a "reagent") contains a liposome composition containing a first liposome having a phospholipid layer, a second liposome having a phospholipid layer of a different composition from that of the first liposome, and a tissue factor. The tissue factor is associated with the phospholipid layer of at least one of the first liposome and the second liposome. The first liposome contains a phosphatidylcholine compound, a phosphatidylethanolamine compound, and a phosphatidylserine compound. The second liposome contains at least one phospholipid selected from the group consisting of a phosphatidylcholine compound and a phosphatidylethanolamine compound.

In the specification, a phosphatidylcholine compound refers to an optionally substituted phosphatidylcholine. A phosphatidylethanolamine compound refers to an optionally substituted phosphatidylethanolamine. A phosphatidylserine compound refers to an optionally substituted phosphatidylserine.

Examples of the substituent of an optionally substituted phosphatidylcholine include, but are not particularly limited to an acyl group having 8 to 20 carbon atoms, preferably 14 to 18 carbon atoms. Examples of the substituent of an optionally substituted phosphatidylethanolamine include, but are not particularly limited to an acyl group having 8 to 20 carbon atoms, preferably 14 to 18 carbon atoms. Example of the substituent of an optionally substituted phosphatidylserine include, but are not particularly limited to an acyl group having 8 to 20 carbon atoms, preferably 14 to 18 carbon atoms. Examples of an acyl group having 8 to 20 carbon atoms include, but are not particularly limited to a lauroyl group, a myristoyl group, a palmitoyl group, a stearoyl group, and an oleoyl group.

Examples of the phosphatidylcholine compound include, but are not particularly limited to phosphatidylcholine, and diacylphosphatidylcholines in which the acyl groups have 8 to 20 carbon atoms, preferably 14 to 18 carbon atoms, such as dilauroylphosphatidylcholine, dimyristoylphosphatidylcholine, dipalmitoylphosphatidylcholine, distearoylphosphatidylcholine, and dioleoylphosphatidylcholine. Among these phosphatidylcholine compounds, preference is given to diacylphosphatidylcholines in which the acyl groups have 8 to 20 carbon atoms, with dioleoylphosphatidylcholine being more preferable.

Examples of the phosphatidylethanolamine compound include, but are not particularly limited to phosphatidylethanolamine, and diacylphosphatidylethanolamines in which the acyl groups have 8 to 20 carbon atoms, preferably 14 to 18 carbon atoms, such as dilauroylphosphatidylethanolamine, dimyristoylphosphatidylethanolamine, dipalmitoylphosphatidylethanolamine, distearoylphosphatidylethanolamine, and dioleoylphosphatidylethanolamine. Among these phosphatidylethanolamine compounds, preference is given to diacylphosphatidylethanolamines in which the acyl groups have 8 to 20 carbon atoms, with dioleoylphosphatidylethanolamine being more preferable.

Examples of the phosphatidylserine compound include, but are not particularly limited to phosphatidylserine, and diacylphosphatidylserines in which the acyl groups have 8 to 20 carbon atoms, preferably 14 to 18 carbon atoms, such as dilauroylphosphatidylserine, dimyristoylphosphatidylserine, dipalmitoylphosphatidylserine, distearoylphosphatidylserine, and dioleoylphosphatidylserine. Among these phosphatidylserine compounds, preference is given to diacylphosphatidylserines in which the acyl groups have 8 to 20 carbon atoms, with dioleoylphosphatidylserine being more preferable.

In the first liposome, the "phosphatidylcholine-to-phosphatidylethanolamine" ratio, which is a ratio of the mass of the phosphatidylcholine compound relative to that of the phosphatidylethanolamine compound, is preferably equal to or above 2.0 from the viewpoint of ensuring an appropriate clotting time and appropriate sensitivity, and preferably less than 3.0, more preferably equal to or below 2.9, from the viewpoint of ensuring an appropriate clotting time and appropriate sensitivity.

Usually, the particle diameter of the first liposome is preferably from 400 to 600 nm from the viewpoint of ensuring an appropriate clotting time and appropriate sensitivity. In the specification, the "particle diameter" value is determined by using a particle size measuring apparatus (manufactured by Spectris Co., Ltd. under a trade name of Zetasizer Nano ZSP) in a particle size determination mode and making measurements at 25° C. by a dynamic light scattering method.

In a reagent according to an embodiment of the present invention, the second liposome has a phospholipid layer containing, as a phospholipid, at least one phospholipid selected from the group consisting of a phosphatidylcholine compound and a phosphatidylethanolamine compound. The second liposome may substantially contain, as a phospholipid, a phosphatidylcholine compound alone or a phosphatidylethanolamine compound alone. Alternatively, the second liposome may substantially contain, as a phospholipid, a phosphatidylcholine compound and a phosphatidylethanolamine compound.

The phosphatidylcholine and phosphatidylethanolamine compounds used in the second liposome are the same as those used in the first liposome.

In cases where the second liposome substantially contains, as a phospholipid, a phosphatidylcholine compound alone, the amount of the phosphatidylcholine compound in the second liposome is preferably equal to or above 20 mg/mL, more preferably equal to or above 40 mg/mL, from the viewpoint of ensuring an appropriate clotting time and appropriate sensitivity, and preferably equal to or below 100 mg/mL from the viewpoint of ensuring an appropriate clotting time and appropriate sensitivity.

In cases where the second liposome substantially contains, as a phospholipid, a phosphatidylethanolamine compound alone, the amount of the phosphatidylethanolamine compound in the second liposome is preferably equal to or above 20 mg/mL, more preferably equal to or above 40 mg/mL, from the viewpoint of ensuring an appropriate clotting time and appropriate sensitivity, and preferably equal to or below 100 mg/mL from the viewpoint of ensuring an appropriate clotting time and appropriate sensitivity.

In cases where the second liposome substantially contains, as a phospholipid, a phosphatidylcholine compound and a phosphatidylethanolamine compound, the total phospholipid amount in the second liposome is preferably equal to or above 20 mg/mL, more preferably equal to or above 40 mg/mL, from the viewpoint of ensuring an appropriate clotting time and appropriate sensitivity, and preferably equal to or below 100 mg/mL from the viewpoint of ensuring an appropriate clotting time and appropriate sensitivity.

In a reagent according to an embodiment of the present invention, the tissue factor is associated with the phospholipid layer of at least one of the first liposome and the second liposome. The phospholipid layer of the first liposome and the phospholipid layer of the second liposome are generally thought to be lipid bilayers. The tissue factor is generally thought to be associated with the phospholipid layer in a state where the tissue factor penetrates through the phospholipid layer. The reagent according to an embodiment of the present invention includes the following:

a reagent containing a liposome composition in which a tissue factor is associated with the phospholipid layer of the first liposome and is not associated with the phospholipid layer of the second liposome;

a reagent containing a liposome composition in which a tissue factor is not associated with the phospholipid layer of the first liposome and is associated with the phospholipid layer of the second liposome; and a reagent containing a liposome composition in which a tissue factor is associated both with the phospholipid layer of the first liposome and with the phospholipid layer of the second liposome.

The tissue factor is thromboplastin, which is also called "factor III of coagulation." The tissue factor includes a naturally derived tissue factor and a recombinant tissue factor. In a reagent according to an embodiment of the present invention, a recombinant tissue factor is preferable because raw materials are easily obtained and stably supplied and because there are small differences in performance between lots, leading to measurement results superior in reproducibility.

As a naturally derived tissue factor, use can be made, for example, of a tissue factor isolated from the brain, placenta, and others of animals of various species using commonly used procedures. Examples of the species of animals from which a naturally derived tissue factor is isolated include, but are not particularly limited to humans, rabbits, bovines, and monkeys and apes. Among these animals, humans are preferable from the viewpoint of more accurately determining human blood clotting time.

A recombinant tissue factor can be obtained, for example, by expressing the recombinant tissue factor in a transgenic organism carrying a cDNA encoding for a tissue factor of an animal of a desired species. A recombinant tissue factor may be one which is commercially available. Among recombinant tissue factors, a recombinant human tissue factor is preferable from the viewpoint of more accurately determining human blood clotting time. Examples of a cDNA encoding for a tissue factor include, but are not particularly limited to ones which encode for a human tissue factor (GenBank Accession No. NM_001993) and a bovine tissue factor (GenBank Accession No. NM_173878). The transgenic organism is obtained, for example, by introducing into a host organism a vector carrying a cDNA encoding for a tissue factor. Examples of the vector include, but are not particularly limited to baculovirus vectors ABv and BEVS. The vector can be selected as appropriate, depending upon the host to be used. Examples of the host include, but are not particularly limited to silkworm larvae, and insect cells such as Sf9 and Sf 21. Introduction of a vector into a host can be performed by methods in accordance with the type of vector to be used. When the vector is a viral vector, the introduction of a viral vector into a host can be accomplished by infection of the host with a recombinant virus derived from the viral vector. The recombinant tissue factor that has been expressed can be obtained from the transgenic organism, for example, by using the following procedures. First, cells of the transgenic organism are disrupted to prepare a cell lysate. The resulting cell lysate is subjected to centrifugation to give a fraction containing the recombinant tissue factor. Then, the resulting fraction can be solubilized to prepare a solution containing the recombinant tissue factor.

Usually, the amount of tissue factor per mg of the phospholipid contained in a reagent according to an embodiment of the present invention is preferably equal to or above 1.6 µg, more preferably equal to or above 5.0 µg, from the viewpoint of ensuring an appropriate clotting time and appropriate sensitivity, and preferably equal to or below 16.7 µg, more preferably equal to or below 12.0 µg, from the viewpoint of ensuring an appropriate clotting time and appropriate sensitivity.

The amount of calcium ions in a reagent according to an embodiment of the present invention can be an amount that is suitable for activating factor VII and allowing the progression of the coagulation reaction. Usually, the amount of calcium ions in a reagent according to an embodiment of the present invention is preferably equal to or above 8 mM, more preferably equal to or above 15 mM, from the viewpoint of ensuring an appropriate clotting time and appropriate sensitivity, and preferably equal to or below 45 mM, more preferably equal to or below 30 mM, from the viewpoint of ensuring an appropriate clotting time and appropriate sensitivity.

A reagent according to an embodiment of the present invention can further contain a buffer from the viewpoint of stably maintaining the tissue factor and calcium ions contained in the reagent. Examples of the buffer include, but are not particularly limited to 4-(2-hydroxyethyl)-1-piperazine ethanesulfonic acid (HEPES) buffer and Tris buffer. The pH of the buffer can be in a range of pH that is suitable for stably maintaining the tissue factor and calcium ions contained in the reagent. The pH of the buffer is preferably equal to or above 7, more preferably 7.5, from the viewpoint of not only ensuring an appropriate clotting time, but also bringing about an improvement in the stability of the reagent, and preferably equal to or below 8.5 from the viewpoint of not only ensuring an appropriate clotting time, but also bringing about an improvement in the stability of the reagent.

A reagent according to an embodiment of the present invention may further contain auxiliaries. Examples of the auxiliaries include, but are not particularly limited to a preservative, an antioxidant, and an excipient. Examples of the preservative include, but are not particularly limited to sodium azide. Examples of the antioxidant include, but are not particularly limited to butylhydroxyanisole. Examples of the excipient include, but are not particularly limited to alanine, sucrose, and mannitol.

A reagent according to an embodiment of the present invention may be a lyophilizate of the reagent, or may be a solution of a lyophilizate of the reagent dissolved in a solvent.

The content of the second liposome relative to the total liposome content in a reagent according to an embodiment of the present invention is preferably 20 to 70 mass %, more preferably 30 to 50 mass %, from the viewpoint of ensuring an appropriate clotting time and appropriate sensitivity.

A reagent according to an embodiment of the present invention contains, as liposomes, a first liposome and a second liposome, wherein the second liposome is composed of at least one phospholipid selected from the group consisting of a phosphatidylcholine compound and a phosphatidylethanolamine compound that are the same as those contained in the first liposome. Accordingly, the reagent will make it possible to ensure measurements that are within an appropriate range of clotting times, specifically ranging from 10.0 to 13.0 seconds, and that have an appropriate international sensitivity index, specifically ranging from 1.0±0.2, when the coagulation of normal plasma is measured. The reagent also has an advantage that in the measurement of clotting time, it is less likely to be affected by coexisting materials.

2. Method for the Production of a Reagent for Prothrombin Time Measurement

A method according to an embodiment of the present invention for the production of a reagent for prothrombin time measurement (hereinafter referred to as a "reagent production method") includes steps of: (A) forming a first liposome having a phospholipid layer, using a phosphatidylcholine compound, a phosphatidylethanolamine compound, and a phosphatidylserine compound; (B) forming a second liposome having a phospholipid layer of a different composition from that of the first liposome, using at least one phospholipid selected from the group consisting of a phosphatidylcholine compound and a phosphatidylethanolamine compound; and (C) allowing a tissue factor to associate with the phospholipid layer of at least one of the first liposome obtained in step (A) and the second liposome obtained in step (B).

In step (A), a first liposome having a phospholipid layer is formed using a phosphatidylcholine compound, a phosphatidylethanolamine compound, and a phosphatidylserine compound.

In step (A), a phosphatidylcholine compound, a phosphatidylethanolamine compound, and a phosphatidylserine compound are first added to chloroform and dissolved therein, thereby to prepare a chloroform solution of the phospholipids. The "phosphatidylcholine-to-phosphatidylethanolamine" ratio (by mass) in the chloroform solution of the phospholipids is preferably equal to or above 2.0 from the viewpoint of ensuring an appropriate clotting time and appropriate sensitivity, and preferably less than 3.0, more preferably equal to or below 2.9, from the viewpoint of ensuring an appropriate clotting time and appropriate sensitivity.

Then, the chloroform is evaporated from the resulting chloroform solution of the phospholipids, thereby to form a phospholipid film. The resulting phospholipid film is swollen in HEPES buffer A (having a composition of 150 mM sodium chloride and 25 mM HEPES (pH 7.35)), thereby to form the first liposome having a phospholipid bilayer. The chloroform can be evaporated, for example, by using an evaporator or the like.

Then, the resulting mixture containing the first liposome is stirred, for example, using a stirrer. The stirring is usually preferably carried out at a speed of not less than 400 rpm, more preferably not less than 450 rpm, from the viewpoint that the components of the mixture are well mixed, and preferably not more than 650 rpm, more preferably not more than 600 rpm, from the viewpoint of preventing the disruption of the liposome. The stirring can be carried out for a period of time sufficient for achieving the swelling of the liposome. The stirring is usually preferably carried out for a period of 45 minutes or longer, more preferably 60 minutes or longer, and preferably 120 minutes or shorter, more preferably 90 minutes or shorter.

Then, the mixture is subjected to ultrasound irradiation to obtain a dispersion. This brings about the formation of a dispersion of the first liposome having a phospholipid bilayer containing the phosphatidylcholine compound, the phosphatidylethanolamine compound, and the phosphatidylserine compound. If necessary, using a membrane with a pore size suitable for obtaining the first liposome having a desired particle diameter, an extruder treatment may be applied to the dispersion, thereby to allow the first liposome to have a uniform particle diameter. The ultrasound irradiation can be carried out at a frequency that allows the first liposome to be well dispersed in the liquid component of the mixture. The frequency of ultrasound waves is usually 37 to 40 kHz. The ultrasound irradiation can be carried out for a period of time that allows the first liposome to be well dispersed in the liquid component of the mixture. The ultrasound irradiation is usually carried out for a period of 5 to 20 minutes.

In step (B), a second liposome having a phospholipid layer of a different composition from that of the first liposome is formed using, as a phospholipid, at least one phospholipid selected from the group consisting of a phosphatidylcholine compound and a phosphatidylethanolamine compound.

In step (B), at least one phospholipid selected from the group consisting of a phosphatidylcholine compound and a phosphatidylethanolamine compound is first added to chloroform and dissolved therein, thereby to prepare a chloroform solution of the phospholipid.

In step (B), the process from the formation of a phospholipid film to the formation of the second liposome is the same as that for the first liposome in step (A). This brings about the formation of a dispersion of the second liposome having a phospholipid bilayer containing at least one phospholipid selected from the group consisting of the phosphatidylcholine compound and the phosphatidylethanolamine compound.

In step (C), the tissue factor is allowed to associate with the phospholipid layer of at least one of the first liposome obtained in step (A) and the second liposome obtained in step (B).

In step (C), the dispersion of the first liposome and/or the dispersion of the second liposome is first mixed into a solution containing the tissue factor, thereby to prepare a mixed liquid of the liposome and the tissue factor. In step (C), a solution containing the tissue factor may be brought into contact with a mixture of the dispersion of the first liposome obtained in step (A) and the dispersion of the second liposome obtained in step (B). Alternatively, in step (C), a solution containing the tissue factor may be brought into contact with the dispersion of the first liposome obtained in step (A) or the dispersion of the second liposome obtained in step (B), followed by bringing the resulting product into contact with the other liposome dispersion that has not been contacted with the tissue factor-containing solution.

Examples of the solvent that can be used to prepare a solution containing the tissue factor include, but are not particularly limited to a Tris-hydrochloric acid buffer A solution (having a composition of 150 mM sodium chloride, 10 mass % glycerol, and 20 mM Tris-hydrochloric acid buffer (pH 8.0)). The amount of tissue factor in a tissue factor-containing solution can be set as appropriate, depending on the type of reagent to be desired. Usually, the amount of tissue factor in a tissue factor-containing solution is preferably equal to or above 0.1 μg/mL, more preferably equal to or above 0.3 μg/mL, from the viewpoint of ensuring an appropriate clotting time and appropriate sensitivity, and preferably equal to or below 1.0 μg/mL, more preferably equal to or below 0.7 μg/mL, from the viewpoint of ensuring an appropriate clotting time and appropriate sensitivity.

When the tissue factor is associated with the phospholipid layer of the first liposome, the volume of a tissue factor-containing solution per mL of the dispersion of the first liposome can be a volume that provides the tissue factor in an amount of 1.6 to 16.7 μg per mg of the first liposome. When the tissue factor is associated both with the phospholipid layer of the first liposome and with the phospholipid layer of the second liposome, the volume of a tissue factor-containing solution per mL of the dispersion of the first liposome can be a volume that provides the tissue factor in an amount of 1.6 to 16.7 μg per mg of the first liposome.

Then, in step (C), the mixed liquid of the liposome and the tissue factor is stirred, for example, using a stirrer or the like. This brings about the formation of a liposome composition in which the tissue factor is associated with at least one of the phospholipid layer of the first liposome and the phospholipid layer of the second liposome. The stirring is carried out preferably at a speed of not less than 850 rpm, more preferably not less than 900 rpm, from the viewpoint of ensuring an appropriate clotting time and appropriate sensitivity, and preferably not more than 1050 rpm, more preferably not more than 1000 rpm, from the viewpoint of ensuring an appropriate clotting time and appropriate sensitivity. The stirring can be carried out for a period of time sufficient for achieving an adequate association of the liposome with the tissue factor. The stirring is usually preferably carried out for a period of 100 hours or longer, more preferably 140 hours or longer, and preferably 300 hours or shorter, more preferably 200 hours or shorter.

To the liposome composition obtained in step (C) is further added a calcium solution, and the resulting mixture is stirred. This yields a reagent for prothrombin time measurement as mentioned above. To the liposome composition obtained in step (C), a stabilizer or the like may be further added, if necessary. The resulting reagent for prothrombin time measurement can be subjected to freeze drying as appropriate. Examples of the calcium solution include, but are not particularly limited to an aqueous solution of calcium chloride. Usually, the concentration of calcium ions in the calcium solution is preferably equal to or above 37.5 mM, more preferably equal to or above 50 mM, from the viewpoint of ensuring an appropriate clotting time and appropriate sensitivity, and preferably equal to or below 75 mM, more preferably equal to or below 62.5 mM, from the viewpoint of ensuring an appropriate clotting time and appropriate sensitivity. The amount of the calcium solution to be added to the liposome composition can be an amount providing an amount of calcium ions in the reagent that is preferably equal to or above 8 mM, more preferably equal to or above 15 mM, and preferably equal to or below 45 mM, more preferably equal to or below 30 mM.

A buffer solution can be further mixed in a reagent according to an embodiment of the present invention from the viewpoint of stably maintaining the tissue factor and calcium ions contained in the reagent.

3. Reagent Kit

The above-described reagent can be provided as a reagent kit including a container enclosing the reagent. An example of a reagent kit according to an embodiment of the present invention is depicted in FIG. 1. The reagent kit 10 depicted in FIG. 1 includes a container 22 having a reagent 21 placed therein, an attached insert 31, and a box 41. The reagent 21 contains a first liposome 101 and a second liposome 102. A phospholipid layer 200 of the first liposome 101 is associated with a tissue factor 210 in a state where the tissue factor penetrates through the phospholipid layer. In this embodiment, the phospholipid layer 200 of the first liposome 101 is composed of dioleoylphosphatidylethanolamine 201, dioleoylphosphatidylcholine 202, and dioleoylphosphatidylserine 203. In this embodiment, the second liposome 102 is formed from a phospholipid layer made up of dioleoylphosphatidylcholine 202. In the embodiment depicted in FIG. 1, the tissue factor 210 is not associated with the phospholipid layer of the second liposome 102; however, the tissue factor 210 may be associated with the phospholipid layer of the second liposome 102. The reagent kit 10 may include, for example, an aqueous solvent for dilution, control plasma, and others. The aqueous solvent can be selected, as appropriate, from aqueous solvents usually used in clinical tests for blood coagulability. Examples of the aqueous solvent include, but are not particularly limited to water and physiological saline. Examples of the control plasma include, but are not particularly limited to normal plasma. The attached insert 31 includes a description of the procedures for measuring prothrombin time using the reagent kit 10. The box 41 houses the container 22 having the reagent 21 placed therein, and the attached insert 31.

EXAMPLES

In the following, "liposome A" refers to the above-described first liposome, and "liposome B" refers to the above-described second liposome. In the examples which follow and others, abbreviations have the following meaning.

<Abbreviations>
DOPE: dioleoylphosphatidylethanolamine
DOPC: dioleoylphosphatidylcholine
DOPS: dioleoylphosphatidylserine
PE: a phosphatidylethanolamine compound
PC: a phosphatidylcholine compound
PS: a phosphatidylserine compound HEPES: 4-(2-hydroxyethyl)-1-piperazine ethanesulfonic acid
ISI: International Sensitivity Index Example 1 and Comparative Example 1

(1) Preparation of Liposome A1

To a recovery flask was added a 25 mg/mL phospholipid-in-chloroform solution A (containing 510 mg of DOPE, 1020 mg of DOPC, and 510 mg of DOPS). Then, the chloroform was evaporated with rotating the recovery flask containing the phospholipid-in-chloroform solution A, using a rotary evaporator. A phospholipid film was thus formed on the inner surface of the recovery flask. The phospholipid film was swollen using 850 mL of HEPES buffer A (having a composition of 150 mM sodium chloride and 25 mM HEPES (pH 7.35)), to obtain a mixture containing a liposome. Then, the mixture was stirred with a stirrer at 500 rpm for 60 minutes. After that, the mixture was exposed to 37 kHz ultrasound irradiation for 15 minutes using an ultrasonic bath sonicator (manufactured by Sharp Corporation under a trade name of UT-306H), to make a solution containing liposome A1. The respective concentrations of DOPE, DOPC, and DOPS in the resulting solution containing liposome A1 were 0.6 mg/mL (for the DOPE concentration), 1.2 mg/mL (for the DOPC concentration), and 0.6 mg/mL (for the DOPS concentration).

(2) Preparation of Liposome B1

A solution containing liposome B1 was prepared in a similar way as in (1), except that 1280 mg of DOPC was used instead of 510 mg of DOPE, 1020 mg of DOPC, and 510 mg of DOPS, and that 800 mL of HEPES buffer A was used to swell the phospholipid film. The concentration of DOPC in the resulting solution containing liposome B1 was 1.6 mg/mL.

(3) Preparation of Reagents for Prothrombin Time Measurement 775 mL of the solution containing liposome A1, which was obtained in (1), 775 mL of the solution containing liposome B1, which was obtained in (2), 310 mL of a 50 μg/mL tissue factor solution, and 1240 mL of HEPES buffer B (having a composition of 22 mM calcium chloride, 1 mM magnesium chloride, 1 mass % sucrose, 0.1 mass % sodium azide, and 25 mM HEPES (pH 7.5)) were mixed. The resulting mixture was stirred at 950 rpm for 8 days with warming to 37° C., resulting in the reconstitution of the liposome and the tissue factor to give a liposome composition. 3 L of the resulting liposome composition and 12 L of HEPES buffer C (having a composition of 0.75 mM alanine, 0.075 mM sucrose, 2.5 mM magnesium chloride, 60 mM calcium chloride, and 25 mM HEPES (pH 7.5)) were mixed. The resulting mixture was charged into vials in an amount of 2 mL per vial. The mixture in the vials was subjected to freeze drying to give a lyophilizate of the reagent for prothrombin time measurement according to Example 1. The content of liposome B1 relative to the total liposome content in the reagent according to Example 1 was 40 mass %.

775 mL of the solution containing liposome A1, which was obtained in (1), 775 mL of HEPES buffer A, 310 mL of a 50 μg/mL tissue factor solution, and 1240 mL of HEPES buffer B were mixed. The resulting mixture was stirred at 950 rpm for 8 days with warming to 37° C., resulting in the reconstitution of the liposome and the tissue factor to give a liposome composition. 3 L of the resulting liposome composition and 12 L of HEPES buffer C were mixed. The resulting mixture was charged into vials in an amount of 2 mL per vial. The mixture in the vials was subjected to freeze drying to give a lyophilizate of the reagent for prothrombin time measurement according to Comparative Example 1.

(4) Determination of Clotting Time and Calculation of ISI

Samples from three lots of the reagent for prothrombin time measurement obtained in (3) were each re-dissolved in 4 mL purified water to prepare reagent solutions.

In a coagulation analyzer (manufactured by SYSMEX CORPORATION under a trade name of CS-2000i), 50 μL specimens were incubated at 37° C. for 1 to 2 minutes. Then, 100 μL of each of the reagent solutions was added to one of the specimens in the coagulation analyzer. After that, the change in the amount of transmitted light at a wavelength of 660 nm was determined for the resulting mixed measurement samples, using the coagulation analyzer. As the specimens, use was made of control plasma (manufactured by Precision BioLogic Inc. under a trade name of CRYOcheck Pooled Normal Plasma) and calibrator plasma (manufactured by Technoclone under a trade name of AK Calibrant).

The measurement value of the clotting time of the calibrator plasma was used to determine ISI values for the measurement samples according to Formula (I), which is represented by: ISI=[ISI when a standard reagent was used]×[the slope of a line obtaining by plotting (logarithms of clotting times of the calibrator when a reagent to be analyzed was used) and (logarithms of clotting times of the calibrator when the standard reagent was used)].

In Table 1 are shown the results of analysis of the clotting times and ISI values when the reagents for prothrombin time measurement according to Example 1 and Comparative Example 1 were used.

TABLE 1

|  | Clotting time (sec) | ISI |
| --- | --- | --- |
| Example 1 | 10.7 | 1.01 |
| Comparative Example 1 | 8.4 | 1.34 |

The results shown in Table 1 have revealed that when the reagent for prothrombin time measurement according to Example 1 was used, the clotting time of the control plasma fell within an appropriate range of clotting times (from 10.0 to 13.0 seconds). In contrast, the results shown in Table 1 have revealed that when the reagent for prothrombin time measurement according to Comparative Example 1 was used, the clotting time of the control plasma was outside an appropriate range of clotting times (from 10.0 to 13.0 seconds).

The phospholipid composition of liposome A in the reagent for prothrombin time measurement according to Example 1 was the same as that of the liposome in the reagent for prothrombin time measurement according to Comparative Example 1. However, the reagent for prothrombin time measurement according to Example 1 contained two types of liposomes which were different in the phospholipid composition, while the reagent for prothrombin time measurement according to Comparative Example 1 contained one type of liposome. Therefore, from these results, it has turned out that an appropriate clotting time cannot be ensured even when a liposome having the same phospholipid composition as that of liposome A in the reagent for prothrombin time measurement according to Example 1 is used alone.

The results shown in Table 1 have also revealed that when the reagent for prothrombin time measurement according to Example 1 was used, the ISI value fell within an appropriate ISI range (1.0±0.2). In contrast, the results shown in Table 1 have revealed that when the reagent for prothrombin time measurement according to Comparative Example 2 was used, the ISI value was 1.34, which represents a great departure from the appropriate ISI range. Therefore, it has turned out that the reagent for prothrombin time measurement according to Comparative Example 2 does not have properties suitable for practical use.

From the above-described results, it has been found that the reagent for prothrombin time measurement according to Example 1 can ensure measurements that are within an appropriate range of clotting times and have an appropriate ISI.

Example 2 and Comparative Example 2

(1) Preparation of Liposome A2

A phospholipid-in-chloroform solution A containing 15 mg of DOPE, 30 mg of DOPC, and 15 mg of DOPS was placed in a glass container. Then, the chloroform was evaporated with rotating the glass container containing the phospholipid-in-chloroform solution A, using a rotator (manufactured by AS ONE Corporation under a trade name of MIX ROTOR VMR-5R). A phospholipid film was thus formed on the inner surface of the glass container. The phospholipid film was swollen using 25 mL of HEPES buffer A to obtain a mixture containing liposome A2. Then, the mixture was stirred with a stirrer at 500 rpm for 60 minutes. After that, the mixture was exposed to ultrasound irradiation for 15 minutes using an ultrasonic bath sonicator (manufactured by Sharp Corporation under a trade name of UT-306H), to make a solution containing liposome A2. The respective concentrations of DOPE, DOPC, and DOPS in the resulting solution containing liposome A2 were 0.6 mg/mL (for the DOPE concentration), 1.2 mg/mL (for the DOPC concentration), and 0.6 mg/mL (for the DOPS concentration).

(2) Preparation of Liposome B2

A solution containing liposome B2 was prepared in a similar way as in (1), except that 40 mg of DOPC was used instead of 15 mg of DOPE, 30 mg of DOPC, and 15 mg of DOPS. The concentration of DOPC in the resulting solution containing liposome B2 was 1.6 mg/mL.

(3) Preparation of Reagents for Prothrombin Time Measurement 20 mL of the solution containing liposome A2, which was obtained in (1), 20 mL of the solution containing liposome B2, which was obtained in (2), 8 mL of a 50 μg/mL tissue factor solution, and 32 mL of HEPES buffer B were mixed. The resulting mixture was stirred at 650 rpm with warming to 37° C., resulting in the reconstitution of the liposome and the tissue factor to give a liposome composition. 80 mL of the resulting liposome composition and 320 mL of HEPES buffer C were mixed. The resulting mixture was charged into vials in an amount of 2 mL per vial. The mixture in the vials was subjected to freeze drying to give a lyophilizate of the reagent for prothrombin time measurement according to Example 2. The content of liposome B2 relative to the total liposome content in the reagent according to Example 2 was 40 mass %.

20 mL of the solution containing liposome A2, which was obtained in (1), and 8 mL of a 50 μg/mL tissue factor solution were added to 32 mL of HEPES buffer B. The resulting mixture was stirred at 650 rpm with warming to 37° C., resulting in the reconstitution of the liposome and the tissue factor to give a liposome composition. 60 mL of the resulting liposome composition, 20 mL of HEPES buffer A, and 320 mL of HEPES buffer C were mixed. The resulting mixture was charged into vials in an amount of 2 mL per vial. The mixture in the vials was subjected to freeze drying to give a lyophilizate of the reagent for prothrombin time measurement according to Comparative Example 2.

(4) Effects of Triglyceride on Clotting Time

Clotting times were measured in a similar way as described in (4) in the section under Example 1 and Comparative Example 1, except that the reagents for prothrombin time measurement according to Example 2 and Comparative Example 2 were used and specimens containing triglyceride or containing no triglyceride were used. Then, percent changes of the clotting times of specimens containing triglyceride relative to the specimen containing no triglyceride were determined. The specimens containing triglyceride were prepared as follows. First, normal plasma (manufactured by SYSMEX CORPORATION under a trade name of Coagtrol IX) and a triglyceride-containing solution (manufactured by NIHON PHARMACEUTICAL CO., LTD. under a trade name of INTRAFAT INJECTION 20%) were mixed such that the ratio (by volume) of normal plasma/triglyceride was 9.5/0.5, to make a solution of sample A. In addition, normal plasma and physiological saline were mixed such that the ratio (by volume) of normal plasma/physiological saline was 9.5/0.5, to make a solution of sample B. Then, the solutions of samples A and B were mixed such that the ratio (by volume) of sample A/sample B was 1/9, to make a specimen having a triglyceride concentration of 100 mg/dL. Further, the solutions of samples A and B were mixed such that the ratio (by volume) of sample A/sample B was 1/4, to make a specimen having a triglyceride concentration of 200 mg/dL. The solution of sample B was used as the specimen containing no triglyceride, that is, a specimen having a triglyceride concentration of 0 mg/dL.

Figure 2:
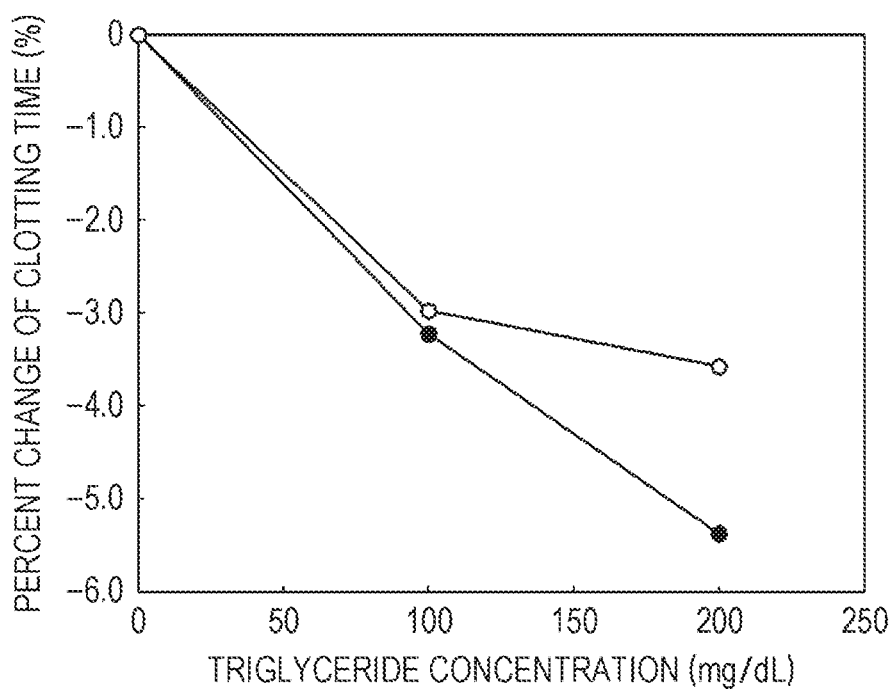
FIG. 2 is a graph showing a relationship between the percent change of clotting time and the concentration of triglyceride when the reagents for prothrombin time measurement according to Example 2 and Comparative Example 2 were used.

In FIG. 2 are shown the results of analysis of the relationship between the percent change of clotting time and the concentration of triglyceride when the reagents for prothrombin time measurement according to Example 2 and Comparative Example 2 were used. In the graph, open circles represent the relationship between the percent change of clotting time and the concentration of triglyceride when the reagent for prothrombin time measurement according to Example 2 was used, and closed circles when the reagent for prothrombin time measurement according to Comparative Example 2 was used.

The results shown in FIG. 2 have revealed that percent changes of clotting time when the reagent for prothrombin time measurement according to Example 2 was used were smaller than those when the reagent for prothrombin time measurement according to Comparative Example 2 was used. Therefore, from these results, it has turned out that a reagent for prothrombin time measurement containing, as liposomes, liposome A, and liposome B composed of a PC that is the same as that contained in the liposome A is less likely to be affected by triglyceride, which is a coexisting substance contained in plasma.

(5) Effects of Bilirubin F Concentration on Clotting Time

Clotting times were measured in a similar way as described in (4) in the section under Example 1 and Comparative Example 1, except that the reagents for prothrombin time measurement according to Example 2 and Comparative Example 2 were used and specimens containing bilirubin F were used. Then, percent changes of the clotting times of the specimens containing bilirubin F relative to a specimen containing no bilirubin F were determined. The specimens containing bilirubin F were prepared as follows. First, normal plasma (manufactured by SYSMEX CORPORATION under a trade name of Coagtrol IX) and a bilirubin F containing-solution (manufactured by SYSMEX CORPORATION under a trade name of Interfering Check A plus) were mixed such that the ratio (by volume) of normal plasma/bilirubin F was 8/2, to make a solution of sample A. In addition, normal plasma and physiological saline were mixed such that the ratio (by volume) of normal plasma/physiological saline was 8/2, to make a solution of sample B. Then, the solutions of samples A and B were mixed such that the ratio (by volume) of sample A/sample B was as shown in Table 2, to make specimens containing bilirubin F. The solution of sample B was used as the specimen containing no bilirubin F, that is, a specimen having a bilirubin F concentration of 0 mg/dL.

TABLE 2

| Bilirubin F concentration (mg/mL) | 0 | 14.8 | 29.6 | 44.4 | 59.2 | 74.0 |
|---|---|---|---|---|---|---|
| Sample A/sample B (by volume) | 0/10 | 2/8 | 4/6 | 6/4 | 8/2 | 10/0 |

Figure 3:
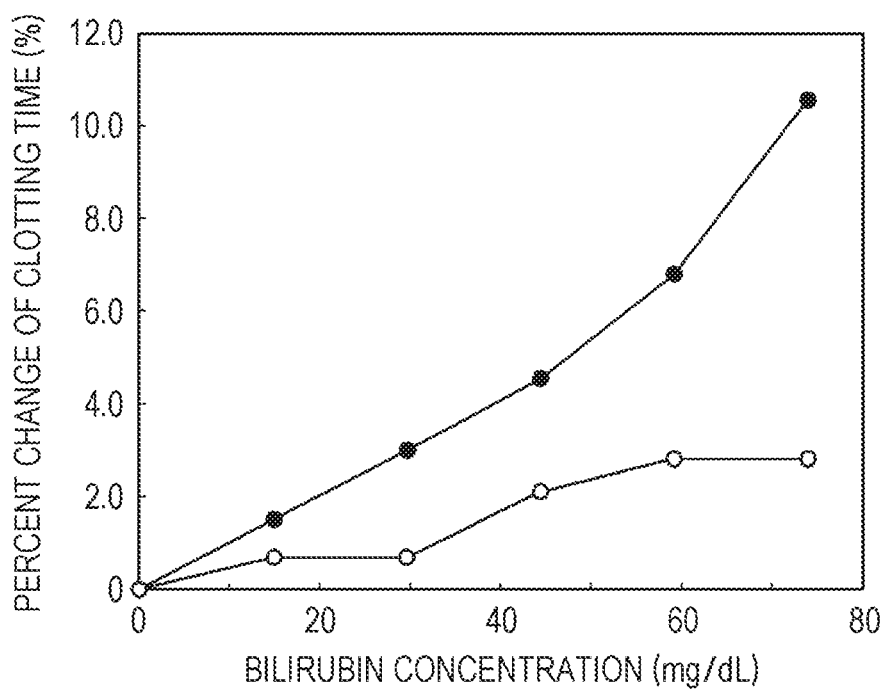
FIG. 3 is a graph showing a relationship between the percent change of clotting time and the concentration of bilirubin F when the reagents for prothrombin time measurement according to Example 2 and Comparative Example 2 were used.

In FIG. 3 are shown the results of analysis of the relationship between the percent change of clotting time and the concentration of bilirubin F when the reagents for prothrombin time measurement according to Example 2 and Comparative Example 2 were used. In the graph, open circles represent the relationship between the percent change of clotting time and the concentration of bilirubin F when the reagent for prothrombin time measurement according to Example 2 was used, and closed circles when the reagent for prothrombin time measurement according to Comparative Example 2 was used.

The results shown in FIG. 3 have revealed that percent changes of clotting time when the reagent for prothrombin time measurement according to Example 2 was used were smaller than those when the reagent for prothrombin time measurement according to Comparative Example 2 was used. Therefore, from these results, it has turned out that a reagent for prothrombin time measurement containing, as liposomes, liposome A, and liposome B composed of a PC that is the same as that contained in the liposome A is less likely to be affected by bilirubin F, which is a coexisting substance contained in plasma.

Examples 3 to 7 and Comparative Example 3

(1) Preparation of Liposomes A3 and A4

A phospholipid-in-chloroform solution A containing 15 mg of DOPE, 30 mg of DOPC, and 15 mg of DOPS was placed in a glass container. Then, the chloroform was evaporated with rotating the glass container containing the phospholipid-in-chloroform solution A, using a rotator (manufactured by AS ONE Corporation under a trade name of MIX ROTOR VMR-5R). A phospholipid film was thus formed on the inner surface of the glass container. The phospholipid film was swollen using 25 mL of HEPES buffer A to obtain a mixture containing liposome A3. Then, the mixture was stirred with a stirrer at 500 rpm for 60 minutes. After that, the mixture was exposed to ultrasound irradiation for 15 minutes using an ultrasonic bath sonicator (manufactured by Sharp Corporation under a trade name of UT-306H), to make a solution containing liposome A3. The respective concentrations of DOPE, DOPC, and DOPS in the resulting solution containing liposome A3 were 0.6 mg/mL (for the DOPE concentration), 1.2 mg/mL (for the DOPC concentration), and 0.6 mg/mL (for the DOPS concentration).

A solution containing liposome A4 was prepared in a similar way as in the preparation of liposome A3, except that 15 mg of DOPE, 70 mg of DOPC, and 15 mg of DOPS were used instead of 15 mg of DOPE, 30 mg of DOPC, and 15 mg of DOPS. The respective concentrations of DOPE, DOPC, and DOPS in the resulting solution containing liposome A4 were 0.6 mg/mL (for the DOPE concentration), 2.8 mg/mL (for the DOPC concentration), and 0.6 mg/mL (for the DOPS concentration).

(2) Preparation of Liposomes B3 to B7

A solution containing liposome B3 was prepared in a similar way as in the preparation of liposome A3 described in (1), except that 20 mg of DOPC was used instead of 15 mg of DOPE, 30 mg of DOPC, and 15 mg of DOPS. The concentration of DOPC in the resulting solution containing liposome B3 was 0.8 mg/mL.

A solution containing liposome B4 was prepared in a similar way as in the preparation of liposome A3 described in (1), except that 40 mg of DOPC was used instead of 15 mg of DOPE, 30 mg of DOPC, and 15 mg of DOPS. The concentration of DOPC in the resulting solution containing liposome B4 was 1.6 mg/mL.

A solution containing liposome B5 was prepared in a similar way as in the preparation of liposome A3 described in (1), except that 60 mg of DOPC was used instead of 15 mg of DOPE, 30 mg of DOPC, and 15 mg of DOPS. The concentration of DOPC in the resulting solution containing liposome B5 was 2.4 mg/mL.

A solution containing liposome B6 was prepared in a similar way as in the preparation of liposome A3 described in (1), except that 80 mg of DOPC was used instead of 15 mg of DOPE, 30 mg of DOPC, and 15 mg of DOPS. The concentration of DOPC in the resulting solution containing liposome B6 was 3.2 mg/mL.

A solution containing liposome B7 was prepared in a similar way as in the preparation of liposome A3 described in (1), except that 100 mg of DOPC was used instead of 15 mg of DOPE, 30 mg of DOPC, and 15 mg of DOPS. The concentration of DOPC in the resulting solution containing liposome B7 was 4.0 mg/mL.

(3) Preparation of Reagents for Prothrombin Time Measurement 20 mL of the solution containing liposome A1, 8 mL of a 50 µg/mL tissue factor solution, and 32 mL of HEPES buffer B were mixed. The resulting mixture was stirred at 650 rpm with warming to 37° C., resulting in the reconstitution of the liposome and the tissue factor to give a liposome composition. 60 mL of the resulting liposome composition, 20 mL of the solution containing liposome B3, and 320 mL of HEPES buffer C were mixed. The resulting mixture was charged into vials in an amount of 2 mL per vial. The mixture in the vials was subjected to freeze drying to give a lyophilizate of the reagent for prothrombin time measurement according to Example 3. The content of liposome B3 relative to the total liposome content in the reagent according to Example 3 was 25 mass %.

Reagents for prothrombin time measurement according to Examples 4 to 7 were prepared in a similar way as in Example 3, except that the solution containing liposome B3 was replaced with the solution containing liposome B4 (Example 4), B5 (Example 5), B6 (Example 6), or B7 (Example 7). The content of liposome B4 relative to the total liposome content in the reagent according to Example 4 was 40 mass %. The content of liposome B5 relative to the total liposome content in the reagent according to Example 5 was 50 mass %. The content of liposome B6 relative to the total liposome content in the reagent according to Example 6 was 57 mass %. The content of liposome B7 relative to the total liposome content in the reagent according to Example 7 was 63 mass %.

20 mL of the solution containing liposome A2, 8 mL of a 50 µg/mL tissue factor solution, 20 mL of HEPES buffer A, and 32 mL of HEPES buffer B were mixed. The resulting mixture was stirred at 650 rpm with warming to 37° C., resulting in the reconstitution of the liposome and the tissue factor to give a liposome composition. 80 mL of the resulting liposome composition and 320 mL of HEPES buffer C were mixed. The resulting mixture was charged into vials in an amount of 2 mL per vial. The mixture in the vials was subjected to freeze drying to give a lyophilizate of the reagent for prothrombin time measurement according to Comparative Example 3.

(4) Determination of Clotting Time and Calculation of ISI

Clotting times were measured and ISI values were calculated in a similar way as described in (4) in the section under Example 1 and Comparative Example 1, except that the reagents for prothrombin time measurement according to Examples 3 to 7 and Comparative Example 3 were used.

In Table 3 are shown the results of analysis of the clotting times and ISI values when the reagents for prothrombin time measurement according to Examples 3 to 7 and Comparative Example 3 were used.

TABLE 3

|  | Clotting time (sec) | ISI |
|---|---|---|
| Example 3 | 10.7 | 1.07 |
| Example 4 | 10.7 | 1.061 |
| Example 5 | 10.7 | 1.064 |
| Example 6 | 11 | 1.058 |
| Example 7 | 11 | 1.072 |
| Comparative Example 3 | 15.6 | 0.904 |

The results shown in Table 3 have revealed that when the reagents for prothrombin time measurement according to Examples 3 to 7 which contained liposome B containing DOPC as a phospholipid were used, both the clotting times and the ISI values were within their respective appropriate ranges, regardless of the content of DOPC in liposome B contained in the reagents. However, it has been revealed that when the reagent for prothrombin time measurement according to Comparative Example 3 which did not contain liposome B containing DOPC as a phospholipid and in which liposome A had a high DOPC content was used, the ISI value was outside the appropriate ISI range. Therefore, from these results, it has turned out that an appropriate clotting time and an appropriate ISI value can be ensured by a reagent for prothrombin time measurement containing, as liposomes, liposome A, and liposome B composed of a PC that is the same as that contained in the liposome A.

Examples 8 to 10 and Comparative Example 4

(1) Preparation of Liposome A5

A phospholipid-in-chloroform solution A containing 15 mg of DOPE, 30 mg of DOPC, and 15 mg of DOPS was placed in a glass container. Then, the chloroform was evaporated with rotating the glass container containing the phospholipid-in-chloroform solution A, using a rotator (manufactured by AS ONE Corporation under a trade name of MIX ROTOR VMR-5R). A phospholipid film was thus formed on the inner surface of the glass container. The phospholipid film was swollen using 25 mL of HEPES buffer A to obtain a mixture containing liposome A5. Then, the mixture was stirred with a stirrer at 500 rpm for 60 minutes. After that, the mixture was exposed to ultrasound irradiation for 15 minutes using an ultrasonic bath sonicator (manufactured by Sharp Corporation under a trade name of UT-306H), to make a solution containing liposome A5. The respective concentrations of DOPE, DOPC, and DOPS in the resulting solution containing liposome A5 were 0.6 mg/mL (for the DOPE concentration), 1.2 mg/mL (for the DOPC concentration), and 0.6 mg/mL (for the DOPS concentration).

(2) Preparation of Liposomes B8 to B11

A solution containing liposome B8 was prepared in a similar way as in the preparation of liposome A5 described in (1), except that 40 mg of DOPE was used instead of 15 mg of DOPE, 30 mg of DOPC, and 15 mg of DOPS. The concentration of DOPE in the resulting solution containing liposome B8 was 1.6 mg/mL.

A solution containing liposome B9 was prepared in a similar way as in the preparation of liposome A5 described in (1), except that 20 mg of DOPE and 20 mg of DOPC were used instead of 15 mg of DOPE, 30 mg of DOPC, and 15 mg of DOPS. The respective concentrations of DOPE and DOPC in the resulting solution containing liposome B9 were 0.8 mg/mL and 0.8 mg/mL.

A solution containing liposome B10 was prepared in a similar way as in the preparation of liposome A5 described in (1), except that 40 mg of DOPC was used instead of 15 mg of DOPE, 30 mg of DOPC, and 15 mg of DOPS. The concentration of DOPC in the resulting solution containing liposome B10 was 1.6 mg/mL.

A solution containing liposome B11 was prepared in a similar way as in the preparation of liposome A5 described in (1), except that 40 mg of DOPS was used instead of 15 mg of DOPE, 30 mg of DOPC, and 15 mg of DOPS. The concentration of DOPS in the resulting solution containing liposome B11 was 1.6 mg/mL.

(3) Preparation of Reagents for Prothrombin Time Measurement 20 mL of the solution containing liposome A5, which was obtained in (1), 20 mL of the solution containing liposome B8, which was obtained in (2), 8 mL of a 50 µg/mL tissue factor solution, and 32 mL of HEPES buffer B were mixed. The resulting mixture was stirred at 950 rpm for 8 days with warming to 37° C., resulting in the reconstitution of the liposome and the tissue factor to give a liposome composition. 80 mL of the resulting liposome composition and 320 mL of HEPES buffer C were mixed. The resulting mixture was charged into vials in an amount of 2 mL per vial. The mixture in the vials was subjected to freeze drying to give a lyophilizate of the reagent for prothrombin time measurement according to Example 8. The content of liposome B8 relative to the total liposome content in the reagent according to Example 8 was 40 mass %.

Reagents for prothrombin time measurement according to Examples 9 to 10 and Comparative Example 4 were prepared in a similar way as in Example 8, except that the solution containing liposome B8 was replaced with the solution containing liposome B9 (Example 9), B10 (Example 10), or B11 (Comparative Example 4). The content of liposome B9 relative to the total liposome content in the reagent according to Example 9 was 40 mass %. The content of liposome B10 relative to the total liposome content in the reagent according to Example 10 was 40 mass %. The content of liposome B11 relative to the total liposome content in the reagent according to Comparative Example 4 was 40 mass %.

(4) Determination of Clotting Time and Calculation of ISI

Clotting times were measured and ISI values were calculated in a similar way as described in (4) in the section under Example 1 and Comparative Example 1, except that the reagents for prothrombin time measurement according to Examples 8 to 10 and Comparative Example 4 were used.

In Table 4 are shown the results of analysis of clotting times and ISI values when the reagents for prothrombin time measurement according to Examples 8 to 10 and Comparative Example 4 were used.

TABLE 4

|  | Clotting time (sec) | ISI |
| --- | --- | --- |
| Example 8 | 12.9 | 1.096 |
| Example 9 | 11.1 | 1.042 |
| Example 10 | 11 | 1.058 |
| Comparative Example 4 | 9.2 | 1.376 |

The results shown in Table 4 have revealed that when the reagents for prothrombin time measurement in which the phospholipid composing liposome B was DOPE alone (Example 8), a mixture of DOPC and DOPE (Example 9), or DOPC alone (Example 10) were used, both the clotting times and the ISI values were within their respective appropriate ranges. Therefore, from these results, it has turned out that an appropriate clotting time and an appropriate ISI value can be ensured by a reagent for prothrombin time measurement containing, as liposomes, liposome A, and liposome B that is composed of at least one phospholipid selected from the group consisting of a PE and a PC that are the same as those contained in the liposome A.

As has been described above, since the reagent for prothrombin time measurement according to an embodiment of the present invention contains a first liposome and a second liposome that is composed of at least one phospholipid selected from the group consisting of a phosphatidylcholine compound and a phosphatidylethanolamine compound that are the same those contained in the first liposome A, it is suggested that the reagent can ensure an appropriate clotting time and an appropriate ISI value when the coagulation of normal plasma is measured, and in addition, is less likely to be affected by coexisting substances.

What is claimed is:

1. A reagent for prothrombin time measurement, wherein the reagent contains a liposome composition comprising a first liposome having a phospholipid layer, a second liposome having a phospholipid layer of a different composition from that of the first liposome, and a tissue factor, wherein
the tissue factor is associated with the phospholipid layer of at least one of the first liposome and the second liposome;
the first liposome comprises a phosphatidylcholine compound, a phosphatidylethanolamine compound, and a phosphatidylserine compound; and
the second liposome consists of at least one phospholipid selected from the group consisting of a phosphatidylcholine compound and a phosphatidylethanolamine compound or consists of the tissue factor and at least one phospholipid selected from the group consisting of a phosphatidylcholine compound and a phosphatidylethanolamine compound.

2. The reagent according to claim 1, wherein the ratio of the mass of the phosphatidylcholine compound to that of the phosphatidylethanolamine compound in the first liposome is less than 3.0.

3. The reagent according to claim 1, wherein the content of the second liposome relative to the total liposome content in the reagent is 20 to 70 mass %.

4. The reagent according to claim 1, wherein the phosphatidylcholine compound in the first liposome is a diacylphosphatidylcholine in which acyl groups have 8 to 20 carbon atoms, the phosphatidylethanolamine compound in the first liposome is a diacylphosphatidylethanolamine in which acyl groups have 8 to 20 carbon atoms, and the phosphatidylserine compound in the first liposome is a diacylphosphatidylserine in which acyl groups have 8 to 20 carbon atoms.

5. The reagent according to claim 1, wherein the phosphatidylcholine compound in the first liposome is dioleoylphosphatidylcholine, the phosphatidylethanolamine compound in the first liposome is dioleoylphosphatidylethanolamine, and the phosphatidylserine compound in the first liposome is dioleoylphosphatidylserine.

6. The reagent according to claim 1, wherein the tissue factor is a recombinant tissue factor.

7. The reagent according to claim 6, wherein the recombinant tissue factor is a recombinant human issue factor.

8. The reagent according to claim 1, wherein the reagent further comprises calcium ions.

9. The reagent according to claim 1, wherein the phosphatidylcholine compound in the second liposome is a diacylphosphatidylcholine in which acyl groups have 8 to 20 carbon atoms, and the phosphatidylethanolamine compound in the second liposome is a diacylphosphatidylethanolamine in which acyl groups have 8 to 20 carbon atoms.

10. The reagent according to claim 1, wherein the phosphatidylcholine compound in the second liposome is dioleoylphosphatidylcholine and the phosphatidylethanolamine compound in the second liposome is dioleoylphosphatidylethanolamine.

11. A reagent for prothrombin time measurement, wherein the reagent contains a liposome composition comprising a first liposome having a phospholipid layer, a second liposome having a phospholipid layer of a different composition from that of the first liposome, and a tissue factor, wherein
the tissue factor is associated with the phospholipid layer of at least one of the first liposome and the second liposome;
the first liposome comprises a phosphatidylcholine compound, a phosphatidylethanolamine compound, and a phosphatidylserine compound; and
the second liposome comprises at least one phospholipid selected from the group consisting of a phosphatidylcholine compound and a phosphatidylethanolamine compound, and does not comprise a phosphatidylserine compound.

* * * * *